United States Patent [19]
Monson

[11] Patent Number: 5,902,225
[45] Date of Patent: May 11, 1999

[54] POST FOAMABLE MULTIPLE-SEQUENTIAL-FOAMING COMPOSITION

[76] Inventor: James A. Monson, 65 W. Southington Ave., Worthington, Ohio 43085

[21] Appl. No.: 08/839,932

[22] Filed: Apr. 17, 1997

Related U.S. Application Data

[63] Continuation-in-part of application No. 08/320,861, Oct. 11, 1994, abandoned.

[51] Int. Cl.[6] .............................. B01J 13/00; C09K 3/30; A61K 7/48; A61K 7/15
[52] U.S. Cl. ................................ 516/10; 424/45; 424/47; 424/73; 510/159; 510/406; 514/945; 516/14
[58] Field of Search ........................... 252/307; 514/945; 424/45, 47, 73; 510/159, 406; 516/10

[56] References Cited

U.S. PATENT DOCUMENTS

| | | | |
|---|---|---|---|
| 2,655,480 | 10/1953 | Spitzer et al. | 252/307 |
| 2,995,521 | 8/1961 | Estignard-Bluard | 424/401 |
| 3,072,487 | 1/1963 | Webster | 252/305 |
| 3,131,152 | 4/1964 | Klausner | 252/305 |
| 3,131,153 | 4/1964 | Klausner | 252/305 |
| 3,131,154 | 4/1964 | Klausner | 252/305 |
| 3,541,581 | 11/1970 | Monson | 252/307 |
| 3,557,004 | 1/1971 | Yolles | 424/47 |
| 3,639,568 | 2/1972 | Schmitt | 424/43 |
| 3,728,265 | 4/1973 | Cella et al. | 252/307 |
| 3,728,276 | 4/1973 | Lieberman et al. | 252/305 |
| 3,840,465 | 10/1974 | Knowles et al. | 252/307 |
| 3,919,101 | 11/1975 | Anstett et al. | 252/305 |
| 3,962,150 | 6/1976 | Viola | 510/406 |
| 3,970,584 | 7/1976 | Hart et al. | 252/305 |
| 3,997,467 | 12/1976 | Jederström | 252/305 |
| 4,086,331 | 4/1978 | Neumann | 424/45 |
| 4,105,142 | 8/1978 | Morris, Jr. | 222/158 |

(List continued on next page.)

FOREIGN PATENT DOCUMENTS

| | | |
|---|---|---|
| 5-112427 | 5/1993 | Japan . |
| 6-093126 | 4/1994 | Japan . |
| 6-35373 | 5/1994 | Japan . |
| 1444334 | 7/1976 | United Kingdom . |
| PCT/US93/07032 | 7/1993 | WIPO . |

OTHER PUBLICATIONS

Derwent abstract for Japanese laid open document to Tanaka No. 5–112427 referred to above, AN–93–185145, week 9323.

Derwent abstract for Japanese patent document to Takahashi No. 6–093126 referred to above, AN–94–148041, week 9418.

*Primary Examiner*—Richard D. Lovering
*Assistant Examiner*—Daniel S. Metzmaier
*Attorney, Agent, or Firm*—Jansson, Shupe, Bridge & Munger, Ltd.

[57] ABSTRACT

This invention provides compositions which are dispensed as initial-stage foams and which post-foam upon spreading during use, thereby exhibiting multiple levels of foam. Each such composition includes a foamable utilitarian constituent, a liquid post-foaming agent, and a compressed gas.

38 Claims, 4 Drawing Sheets

U.S. PATENT DOCUMENTS

| | | | |
|---|---|---|---|
| 4,111,827 | 9/1978 | Thompson et al. | 424/47 |
| 4,113,643 | 9/1978 | Thompson et al. | 252/305 |
| 4,122,159 | 10/1978 | Madrange et al. | 424/45 |
| 4,140,648 | 2/1979 | Thompson et al. | 424/47 |
| 4,356,848 | 11/1982 | Spies | 222/514 |
| 4,405,489 | 9/1983 | Sisbarro | 252/315.4 |
| 4,490,279 | 12/1984 | Schmolka | 252/357 |
| 4,495,169 | 1/1985 | Schmolka | 424/47 |
| 4,573,506 | 3/1986 | Paoletti | 141/98 |
| 4,574,052 | 3/1986 | Gupte et al. | 510/120 |
| 4,652,389 | 3/1987 | Moll | 510/279 |
| 4,657,690 | 4/1987 | Grollier et al. | 510/119 |
| 4,663,069 | 5/1987 | Llenado | 510/126 |
| 4,664,835 | 5/1987 | Grollier | 510/119 |
| 4,726,944 | 2/1988 | Osipow et al. | 514/881 |
| 4,750,647 | 6/1988 | Cohen | 222/386.5 |
| 4,761,273 | 8/1988 | Grollier et al. | 424/47 |
| 4,772,427 | 9/1988 | Dawson | 510/158 |
| 4,808,388 | 2/1989 | Buetler et al. | 424/47 |
| 4,834,152 | 5/1989 | Howson et al. | 141/286 |
| 4,836,939 | 6/1989 | Hendrickson et al. | 252/3 |
| 4,871,530 | 10/1989 | Grollier et al. | 424/47 |
| 4,876,083 | 10/1989 | Grollier et al. | 424/47 |
| 4,931,204 | 6/1990 | Ramirez et al. | 424/43 |
| 4,981,238 | 1/1991 | Wenmaekers | 222/103 |
| 4,986,322 | 1/1991 | Chibret et al. | 141/319 |
| 4,996,240 | 2/1991 | Osipow et al. | 521/78 |
| 5,002,680 | 3/1991 | Schmidt et al. | 510/140 |
| 5,027,872 | 7/1991 | Taylor et al. | 141/347 |
| 5,031,675 | 7/1991 | Lindgren | 141/291 |
| 5,112,525 | 5/1992 | Straw | 252/315.3 |
| 5,171,577 | 12/1992 | Griat et al. | 424/47 |
| 5,186,857 | 2/1993 | Ramirez et al. | 424/43 |
| 5,209,565 | 5/1993 | Goncalves | 366/130 |
| 5,221,530 | 6/1993 | Janchitraponvej et al. | 424/47 |
| 5,225,095 | 7/1993 | DiMaio et al. | 252/307 |
| 5,232,632 | 8/1993 | Woo et al. | 510/406 |
| 5,244,468 | 9/1993 | Harris et al. | 8/137 |
| 5,248,495 | 9/1993 | Patterson et al. | 424/73 |
| 5,256,400 | 10/1993 | Friox et al. | 424/45 |
| 5,286,475 | 2/1994 | Louvet et al. | 424/45 |
| 5,290,539 | 3/1994 | Marecki | 222/402.2 |
| 5,300,302 | 4/1994 | Tachon et al. | 424/488 |
| 5,316,054 | 5/1994 | Hall et al. | 141/22 |
| 5,334,325 | 8/1994 | Chaussee | 424/43 |
| 5,451,396 | 9/1995 | Villars | 514/944 |

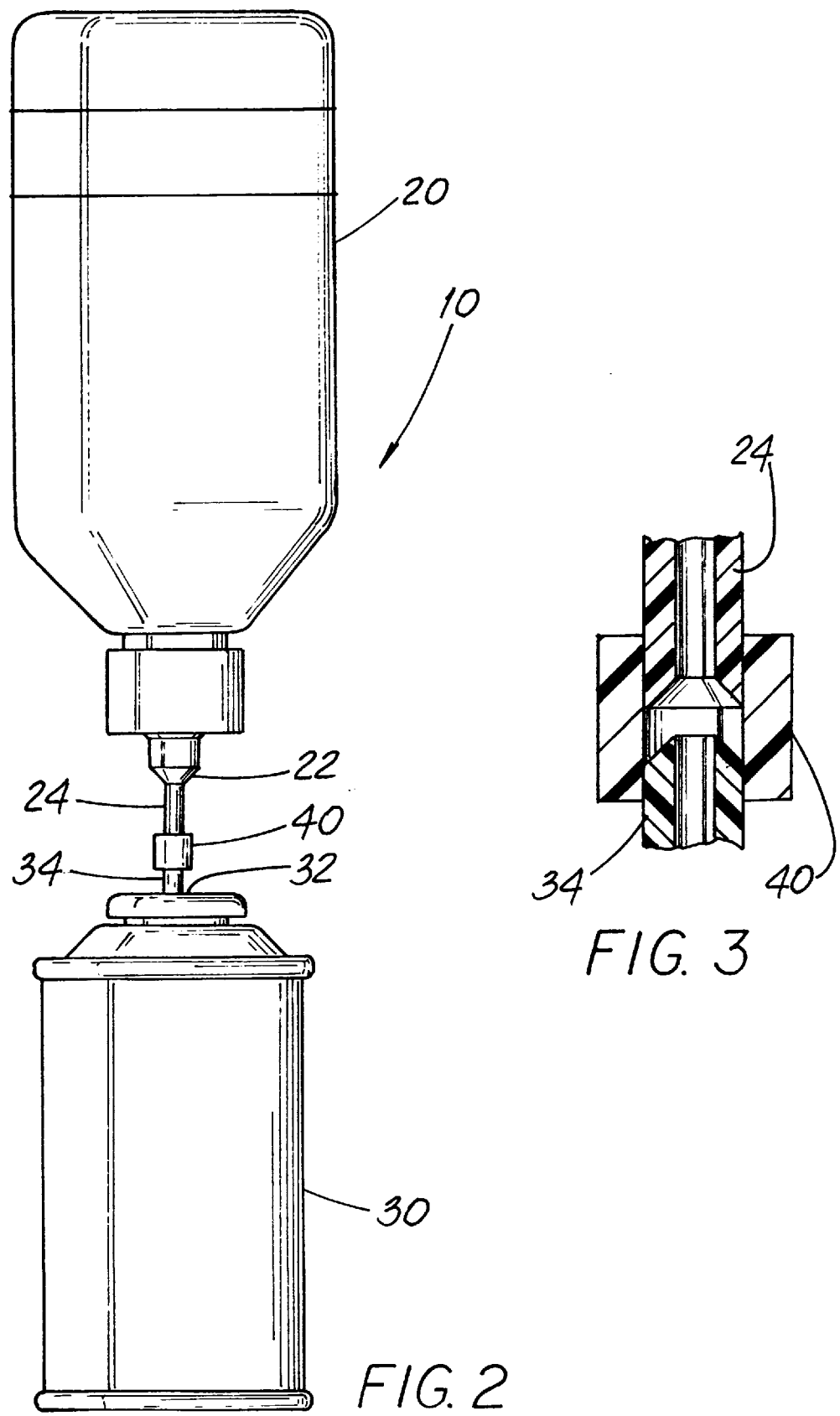

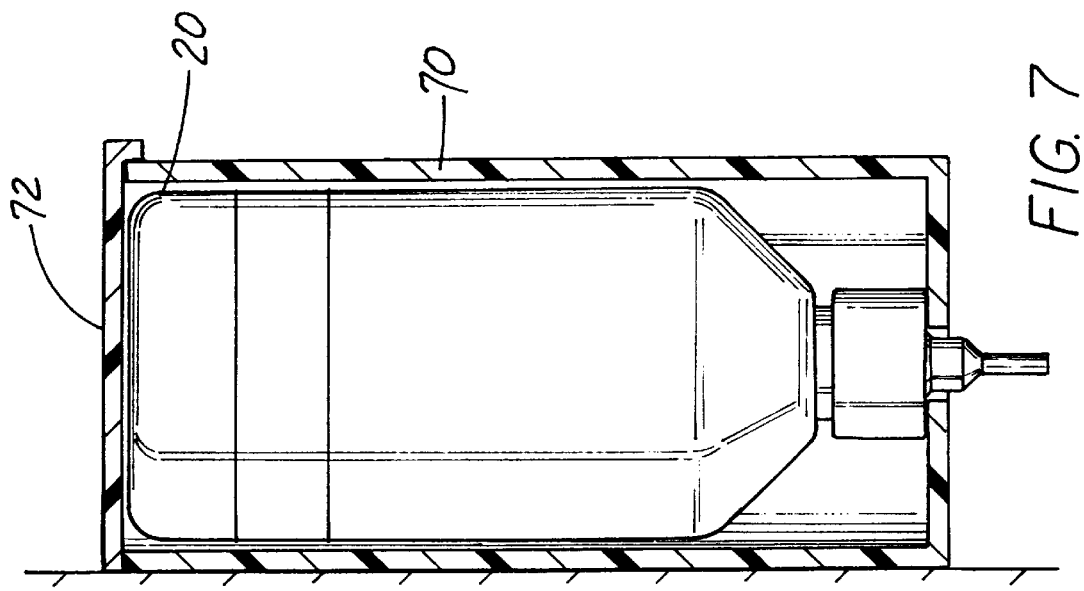
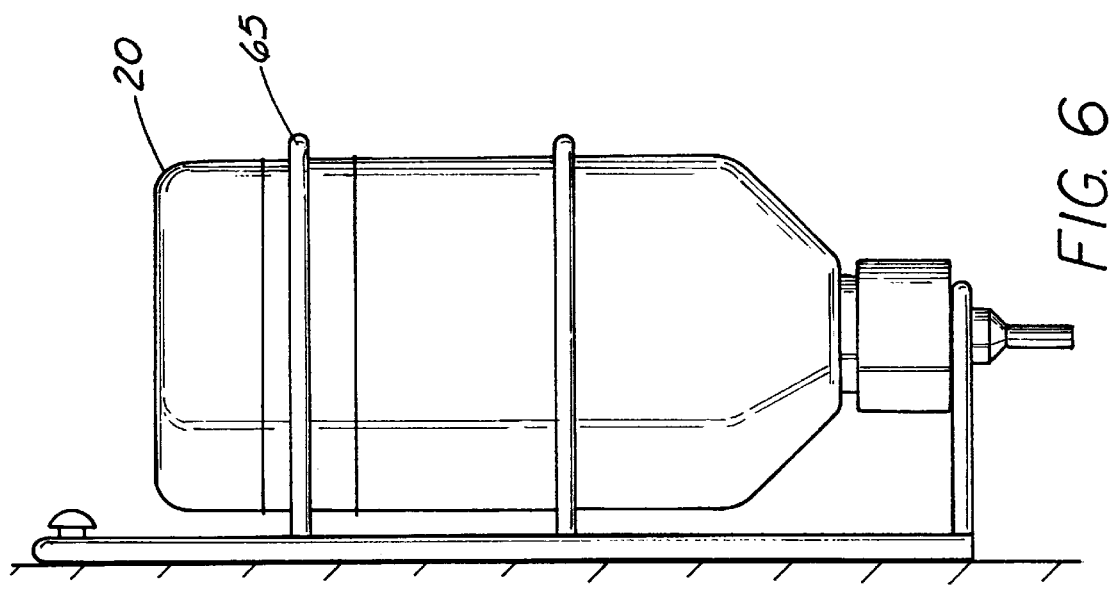

POST FOAMABLE MULTIPLE-SEQUENTIAL-FOAMING COMPOSITION

RELATED APPLICATION

This is a continuation-in-part of Ser. No. 08/320,861, filed Oct. 11, 1994, entitled POST-FOAMABLE FOAM COMPOSITION, now abandoned.

FIELD OF THE INVENTION

This invention is related to the specific field of post-foamable compositions and, more particularly, to post-foamable personal-care and household and industrial cleaning products.

BACKGROUND OF THE INVENTION

Conventional personal-care and household and industrial cleaning products are available in solid, powder, liquid, gel and cream forms. The most common and familiar personal-care and cleaning product on the market today is a bar soap, which produces a lather or foam by agitation with the hands and body. Bar soaps come in a variety of types and are relatively inexpensive. However, problems associated with bar soaps are numerous.

One of the most common problems is the difficulty in "working up" a lather from the bar for spreading. Considerable time and dexterity are usually required. Another problem associated with bar soaps is the inability to maintain sanitary conditions while exposing the bar to multiple uses and multiple users. A bar soap is often viewed as an object used by an entire household, office or other users of a common bathroom or sink. While personal hygiene is just that, personal, soap is considered a "community object." An additional problem associated with bar soaps is maintaining them in a fresh, appealing condition. Soap bars sit in soap dishes and are exposed to moisture where they tend to break down into an unsightly gelatinous state. Additionally, bar soaps tend to cause unsightly residue or "scum" on sink, bath tub and shower surfaces.

In an effort to overcome some of these problems, liquid cleaning and personal-care products were developed. These products are generally available as thick liquids. Examples are shampoos, conditioners, shower gels, liquid soaps and cleaners. These products are relatively slow-foaming and produce very little foam, which is relatively weak and flattens quickly. Additionally, to maintain acceptable levels of foam, repeated use of the products in one grooming or cleaning session is often required. Furthermore, many of these liquid or gel products are subject to a drip or drool factor, whereby after dispensing a portion of the substance remains in the valve of the container and tends to drool after time, leaving an unsightly mess on dispensers and on sink, counter and shower surfaces.

Compositions dispensed as foams overcome some of the shortcomings of bar and liquid products, and are regarded as desirable in part because of an association of foam with cleaning ability. However, even products dispensed as foams often have significant problems related to inadequate characteristics of the foam, as discussed in more detail below.

Post-foaming gel compositions are still another kind of product developed in an effort, among other things, to overcome some of the shortcomings of bar and liquid products. A post-foaming gel composition is typically dispensed from a pressurized barrier package/container in a state where it is substantially free from foaming. When the dispensed gel is spread over the skin, hair or other surface, it gradually post-foams and is thus conveniently transformed into a lathered product without agitation.

One disadvantage associated with post-foaming gel products is that upon dispensing, post-foaming is not easily completed because the gel is not easily spread in an even and fluid manner over the surface to be treated or cleaned. During spreading, the gel tends to clump, pocket, or collect between the fingers and falls off the surface to be cleaned, particularly surfaces that are not horizontal. As a consequence, much of the gel is never transformed through post-foaming into a useful lather. This has been experienced by millions of users of such products.

Post-foaming gel products are generally packaged in rigid pressurized barrier packages/containers with hydrocarbon propellant gases contained therein. Such containers are expensive to manufacture and ship. The propellants which provide the positive pressure needed to aid in the dispensing of the product often do not form an integral part of the composition and are typically compartmentalized from the gel product; such containers are known in the industry as barrier packages because they provide a barrier between the propellants and the composition to be dispensed. Certain propellant gases ultimately released to the atmosphere from such containers have increasingly come under attack because they are environmentally unacceptable. Furthermore, the containers are not readily reusable or recyclable.

Each of the above-noted products suffers from various deficiencies. One of the greatest deficiencies is lack of foam or difficulty in obtaining and maintaining adequate foam levels during use.

In personal care and in household and industrial cleaning, foam and foam stability are associated with cleaning ability, as noted above. The consumer equates a greater foam level with better cleaning ability. In personal care, foams provide a particularly pleasing effect or feel if a rich, slightly wet, creamy foam can be achieved. These foam properties generally require a foam with a fine bubble texture.

In the past, it has been found that foams produced on dispensing from pressurized packages are often either too wet and runny, with limited foam stability, or are too stiff and dry. Neither of these sorts of characteristics provides the essential pleasing feel or texture referred to above. Therefore, it would be an improvement in the art to provide a composition that readily produces an initial rich foam or lather, and continues to produce greater foam levels during the cleansing process during which, of course, the composition is spread over an area much larger than the initial dispensing area.

In summary, a considerable number of deficiencies exist in the art relating to utilitarian compositions and in particular personal-care and cleaning compositions. While bar soaps are inexpensive and convenient, they are lacking in areas of hygiene and sanitation as well as in foam production and maintenance. Although liquid, foam and post-foaming gel products provide more convenience and sanitation, they too lack the optimum foam-producing and foam-maintaining capabilities, and often lack the good spreading ability desired in certain personal-care and cleaning compositions. Additionally, prior art post-foaming gel compositions often prove difficult and expensive to package and use, are often problematic from an environmental standpoint, and are costly.

Thus, there is an ongoing search for compositions which can be spread easily, provide the desired foam characteristics during use while maintaining sufficient foam levels even when spread during use, and are packaged and used in a more environmentally-acceptable manner. Clearly, there is a need for improved and novel personal-care and cleaning compositions that provide a desired creamy, rich foam, maintain foam levels during the spreading which occurs in the cleaning process, are economical, are easily dispensed, and can withstand multiple uses and multiple users while maintaining sanitary conditions and a clean, pleasing appearance.

In particular, there is a need for improved post-foaming products which overcome the foam shortcomings of the post-foaming products of the prior art. There is a need for improved post-foaming products which may be applied and spread easily and while maintaining good foam properties despite and during the spreading and use.

OBJECTS OF THE INVENTION

It is an object of this invention to provide personal-care and cleaning compositions which overcome some of the problems and shortcomings of the prior art.

A further object of the invention is to provide a foaming cleaning composition that can be used multiple times by multiple users while maintaining sanitary conditions.

Another object of this invention is to provide personal-care and cleaning compositions which produce a desirable initial foam as well as increased foam levels during the cleansing process of spreading and dilution.

Another object of this invention is to provide improved post-foamable compositions, particularly improved post-foamable personal-care and household and industrial cleaning products.

Still another object of this invention is to provide improved post-foamable compositions which overcome certain problems and disadvantages of post-foamable gel products.

Another object of this invention is to provide foam products which exhibit multiple levels of foam, including initial foam upon dispensing and post-foaming upon spreading for extended foam during usage.

Still another object of the invention is to provide a foaming cleaning composition that is easily dispensed and for which there is no concern about possible harm to the environment.

These and other important objects will be apparent from the following description and from the drawings.

SUMMARY OF THE INVENTION

This invention relates to novel post-foamable compositions. It overcomes certain well-known problems and deficiencies of the prior products, including those outlined above. An important aspect of the improved post-foamable composition of this invention is that it is a composition which is dispensed as a foam and then, upon the simple act of spreading during normal use, post-foams to quickly produce more foaming, thus providing convenience and extended effective usefulness.

The inventive composition includes a foamable utilitarian constituent, a post-foaming agent and compressed gas. Such a composition exhibits multiple levels or stages of foam and provides for extended foam character throughout the cleaning process. The multiple stages of foam characterizing the invention include, and are referred to herein as, an "initial-stage foam" and a "second-stage foam." As hereafter described and explained, the initial-stage foam is formed upon dispensing and the second-stage foam, having reduced foam density and increased foam volume, is formed by post-foaming during the spreading inherent in use.

In one embodiment, the foamable utilitarian constituent includes a surface active agent. The surface active agent includes nonionic, anionic, amphoteric and cationic surfactants. The specific surface active agents used are dependent on the purpose for which the composition is to be utilized. Generally, the inventive compositions include about 0.1–60% of the utilitarian constituent. Further, the foamable utilitarian constituent can include more than one surface active agent to impart various characteristics to the composition.

The term "utilitarian constituent" is used herein with reference to the composition as ready for dispensing, and sometimes with reference to a concentrate which would thereafter be diluted prior to use. As used herein in defining the invention, the term "utilitarian constituent" refers to the principal "active" ingredient or ingredients together with all diluents, thickeners and other additive components (other than the volatile liquid post-foaming agent and the compressed gas), as described herein, which are used in the composition.

The post-foaming agent causes further foaming of the initial dispensed foam upon the act of continued spreading during normal use. The post-foaming agent of the inventive composition is selected from the group consisting of saturated aliphatic hydrocarbons, halogenated hydrocarbons, and mixtures thereof. The post-foaming agent, which is a liquid or liquefiable in the composition, is typically about 0.5–24% of the novel post-foamable foam composition.

The compressed gas of the composition provides for both dispensing of the composition and initial foaming of the composition when dispensed. The compressed gas is one of the group including carbon dioxide, nitrous oxide, nitrogen, argon, neon, krypton, xenon, helium, and mixtures thereof. Carbon dioxide and nitrous oxide and mixtures are preferable because they are inexpensive and easily accessible. The compressed gas is present in amounts sufficient to provide the composition, when contained in a dispenser, with dispensing pressure. The compressed gas is also present in amounts sufficient to immediately foam the composition when it is dispensed. Typically, to provide both of these functions, the compressed gas should be present in amounts sufficient to provide about 10–60 pounds per square inch gauge (psig) on the composition when it is contained.

The utilitarian constituent of the composition of this invention can further include a diluent, preferably water, and further additives such as emollients, thickeners, fragrances, preservatives, etc. The diluent assists in the foaming and lathering and is used in quantities which, along with the other additives, result in the desired viscosity and concentration for the composition. The composition can include about 16–99.4% diluent; in preferred embodiments about 55–98.5% of the composition is diluent. Appropriate selection and amounts will be apparent to persons skilled in the post-foaming products art who are made familiar with this invention. It is known in the art that post-foaming is controlled in part by viscosity.

As already noted, the composition exhibits multiple sequential stages of foam; the composition is dispensed by the compressed gas as a continuous foam body and, thereafter upon continuous spreading, exhibits further sequential stages of foam. These stages of foam include an initial stage of foam where the utilitarian constituent is foamed by the compressed gas on dispensing. This initial stage of foam has a density of about 0.15%0.90 g/cc. The second stage of foam results from the vaporizing post-foaming agent upon spreading. The second stage of foam has a density of about 0.04–0.30 g/cc. Additional stages of foam are possible including a stage of foam resulting from agitation of the composition on a surface to be cleaned, thereby entraining atmospheric air in the utilitarian constituent. These multiple stages or levels of foam provide for extended foam character.

BRIEF DESCRIPTION OF THE DRAWINGS

FIG. 2, representing an alternative embodiment, is an elevation view of the dispensing container of FIG. 1 shown in conjunction with a concentrate container having the concentrate charged into the dispensing container of FIG. 1.

FIG. 3 is a cross-sectional elevation view showing mating female and male valve stems used respectively with the upright and inverted containers shown in FIG. 2.

FIG. 6 is a side elevation view of an exemplary dispensing container like that of FIG. 1 shown in conjunction with a container mounting rack as for a shower or bath, for example.

FIG. 7 is a cross-sectional side elevation view of an exemplary dispensing container like that of FIG. 1 shown in conjunction with an enclosed container holder for a shower or bath and having a removable top.

DETAILED DESCRIPTIONS OF THE PREFERRED EMBODIMENTS

Figure 1:
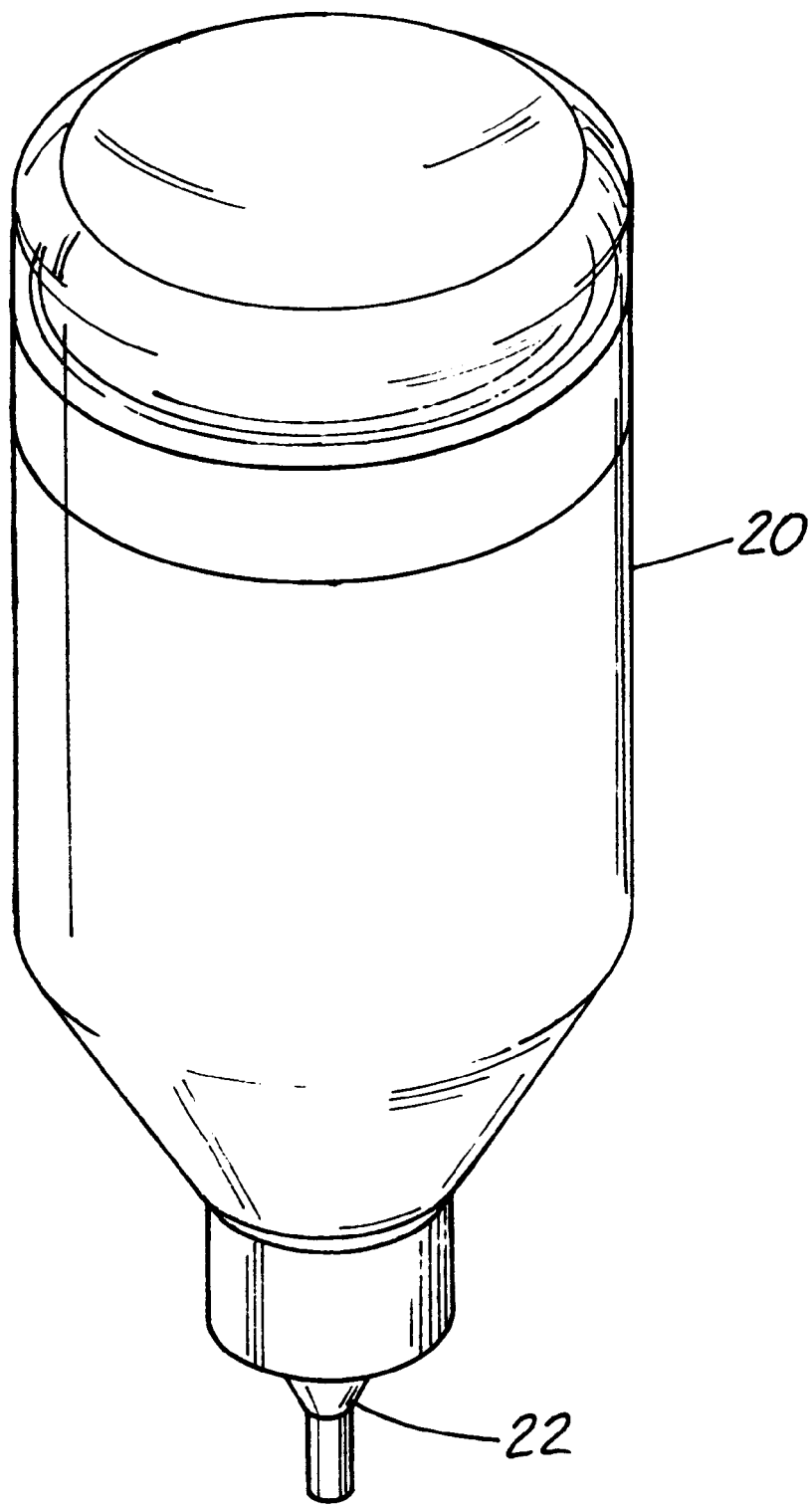
FIG. 1 is a perspective view of an exemplary dispensing container having the inventive post-foaming composition used for bathing or the like therein. Such container is typical of containers used for factory-made forms of the composition.

The present invention is directed to an improvement in post-foaming compositions—namely, post-foamable foam compositions. The post-foamable foam compositions of this invention include a foamable utilitarian constituent, a post-foaming agent and compressed gas, as described in further detail below.

The foamable utilitarian constituent includes the main "active" ingredient of the composition—that which provides the function or purpose of the composition. Highly preferred utilitarian constituents include at least one surface active agent, as is the case when the composition of the invention are personal-care products, such as shampoos, cleansers, shaving products, hand-and-body cleaners and conditioners, or household and industrial cleaners, such as hard-surface cleaners, multi-purpose cleaners, bathroom cleaners and glass cleaners. The utilitarian constituent can be a variety of other products, including food-based as in the area of dairy products, such as cream or cheese-spread products.

The highly preferred utilitarian constituents, which are surface active agents, can include nonionic, anionic, amphoteric and cationic surfactants. When a surface active agent is used alone, nonionic, anionic, or amphoteric surfactants are preferable. When the foamable utilitarian constituent includes a mixture of more than one surface active agent, anionic, nonionic, cationic and amphoteric surfactants can be used. The inventive composition preferably includes about 0.10–60% foamable utilitarian constituent.

Numerous surface active agents or surfactants are known and suitable for use in the composition of the present invention, depending on the function of the composition. A variety of these surface active agents can be found in *McCutcheon's Emulsifiers and Detergents*, 1994. Examples of the numerous suitable anionic surface active agents are alkyl benzene sulfonates in which the alkyl group contains from 9 to 15 carbon atoms, preferably 11 to 14 carbon atoms in straight chain or branches chain configuration; alkyl sulfates obtained by sulfating an alcohol having 8 to 22 carbon atoms, preferably 12 to 16 carbon atoms (the alkyl sulfates have the formula $(ROSO_3)_2M$ here R is the $C_{8-22}$ alkyl group and M is the alkaline earth metal); paraffin sulfonates having 8 to 22 carbon atoms, referably 12 to 16 carbon atoms in the alkyl moiety; olefin sulfonates having 8 to 22 carbon atoms, preferably 12 to 16 carbon atoms; alkyl ether sulfates derived from ethoxylating an alcohol having 8 to 22 carbon atoms, preferably 12 to 16 carbon atoms with 1 to 30, preferably 1 to 12 moles of ethylene oxide and then sulfating; and alkyl glycerol ether sulfonates having 8 to 22 carbon atoms, preferably 12 to 16 carbon atoms in the alkyl moiety.

Examples of some preferred surface active agents suitable for use in body and hand cleaners are ammonium lauryl sulfate, decyl polyglucose, sodium laureth sulfate, decyl polyglucose, ammonium cocoyl isothioniate, and soyamidopropyl betaine.

The post-foaming agent included in the composition causes further foaming of the initial dispensed foam upon the act of continued spreading during normal use. This provides for lasting foam character of the composition and multiple levels or stages of foam, thereby reducing or eliminating the need for multiple applications of the composition during cleaning to maintain foam.

The post-foaming agents are liquids or liquefiable in the composition and include saturated aliphatic hydrocarbons having from 4–6 carbon atoms, such as butanes, preferably isobutane, pentanes, preferably isopentane, hexanes, and partially or wholly halogenated hydrocarbons, such as trichlorotrifluoroethane (Freon 13), and 1,2 dichloro, 1,1,2, 2-tetrafluoroethane (Freon 114). Mixtures of these hydrocarbon and/or halogenated hydrocarbon post-foaming agents are useful for providing the particular vapor pressure desired. An advantage of using mixtures of two or more post-foaming agents is that although the individual agents may have vapor pressures outside the desired range, when combined in the composition, the resulting composition has a vapor pressure within the range of from about 6 to 14 psig at a temperature from about 90 to about 100° F. This temperature range is the most suitable for personal-care products which are used on humans having a body temperature of about 98.6° F. In preferred embodiments, where a mixture of at least two post-foaming agents is utilized, the mixture can include about 10–90% of a first post-foaming agent and about 90–10% of a second post-foaming agent. In one embodiment, the preferred post-foaming agent is a mixture of isobutane and isopentane, which is substantially a liquid in the composition when dispensed. The preferred ratio of the mixture is about 1:3 or 1:4. Post-foaming agents will comprise about 0.50–24% of the total post-foaming foam composition.

The compressed gas of the inventive composition provides two functions. Initially, the compressed gas provides the necessary dispensing pressure required to dispense the composition when contained. The second function of the compressed gas in the composition is to provide the initial foam level (i.e., density). To meet the above requirements, the compressed gas should be present in amounts sufficient to provide about 10–60 psig when freshly sealed in a suitable low pressure, clear PET container. In a preferred embodiment, the compressed gas exerts about 35 psig on the composition when it is contained.

The compressed gas can be any suitable compressed gas known to one of ordinary skill in the art. In preferred embodiments, the compressed gas is one of the group including carbon dioxide, nitrous oxide, nitrogen, argon, neon, krypton, xenon, helium, and mixtures thereof.

The inventive composition can also include a diluent. The diluent is included to assist in foaming and lathering. Additionally, as noted above, the diluent is used in quantities which, along with the other additives, provide the desired viscosity and concentration for the composition. The diluent is preferably one of the group including water, propylene glycol, glycerine, and mixtures thereof; in the most preferred embodiments, the diluent is water. The inventive composition can include about 16–99.4% diluent. In preferred embodiments about 55–98.5% of the composition is diluent.

The composition of the present invention may also contain minor amounts of conventional additional ingredients to impart various desired characteristics to the composition. Examples of suitable additives are thickening agents, coloring agents, perfumes, preservatives, antiseptic agents, antibacterial agents, disinfectants, emollients and humectants. Further, the inventive compositions can include conditioning agents such as glycerine, guar hydroxypropyl trimonium chloride, fatty acid esters, and highly branched hydrocarbons such as those sold by The Permethyl Corporation under the trademark PERMETHYL 104A.

The composition may contain any of a variety of suspending agents or thickening agents for imparting desired viscosity to the composition when contained prior to dispensing. Preferred viscosities of the contained composition are on the order of 4,000–8,000 cps. Examples of suitable thickening agents are carboxy vinyl polymers available from B. F. Goodrich Company under the trademark CARBOPOL, carbomers, sodium polacrylate, hydroxyethyl cellulose, guar gum and xanthum gum.

Figure 4:
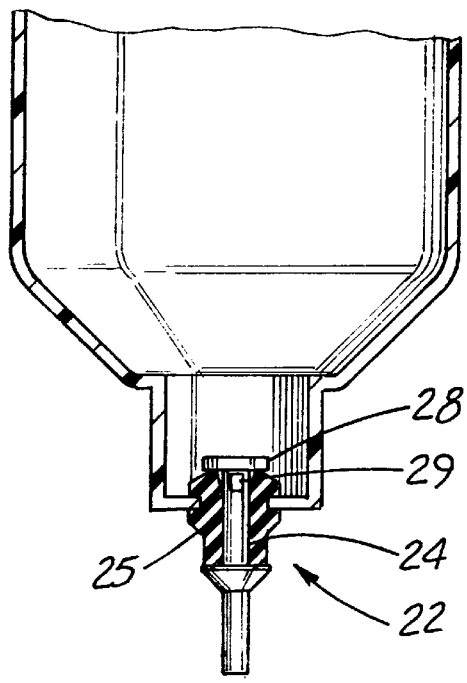
FIG. 4 is a cross-sectional elevation view of a dispensing container like that of FIG. 1 which is free of a removable cap and has a dispensing valve made integrally therewith. Parts are broken away.
Figure 5:
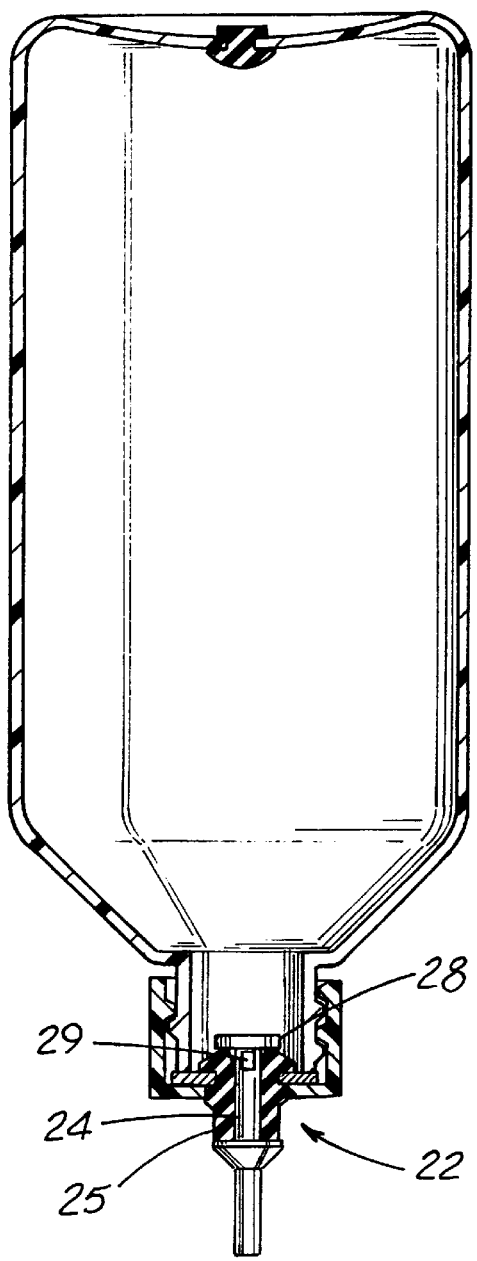
FIG. 5 is a cross-sectional elevation view of another dispensing container like that of FIG. 1 which includes a removable cap having a dispensing valve therewith.

Factory-ready forms of the compositions of the present invention are typically dispensed from a container having a valve arrangement. One embodiment of such a container is shown in FIG. 1. This container is typical of the container usable by a consumer in the shower. This container 20 should be of barrier material to prevent loss of pressure. The barrier material may be a barrier plastic material, metal, glass, or a metal-coated plastic material, or laminated material. In preferred embodiments, the container 20 is translucent or transparent for reasons which will become apparent hereinafter. A preferred material for the container 20 is polyethyleneterepthalate (PET). As can be seen in FIGS. 1, 4, and 5, valve 22 is a valve of the type commonly known in the industry as a "Clayton valve." Valve 22 has a wide diameter hollow stem 24 typical of valves used to dispense product as a continuous foam body rather than as a spray.

The compositions of the present invention can be prepared using various methods. In one embodiment, shown in FIG. 2, the composition is prepared using a novel dispenser system to prepare and dispense the composition. In this embodiment, a first or dispensing container 20 having a valve 22 is provided. As shown in FIGS. 4 and 5, the valve 22 includes a hollow stem 24, a resilient stem retainer 25, a valving member 28 and inlet passages 29 in communication with the hollow passage through the stem. A diluent such as water is in the first container.

A second or concentrate container 30 having a valve 32 is also provided. The valve 32 is similar in arrangement to the valve 22 and also includes a stem 34. This second container 30 includes a concentrate. The concentrate typically includes about 2.0–60% foamable utilitarian constituent, 6–24% post-foaming agent and about 16–72% diluent. The second container 30 can be any known container including barrier packages known to one of ordinary skill in the art. The second container should include a propellant capable of dispensing the concentrate from the second container 30. The propellant should be present in such amounts to provide about 50–80 psig on the concentrate when contained. Any of a variety of propellants can be used so long as the terminal pressure (pressure exerted on the remaining concentrate when the second container is almost empty) is at least about 20 psig. Suitable propellants include the condensable gases including hydrocarbons such as propane, butane, isobutane, and isopentane. Environmentally hazardous halogenated hydrocarbons represented by the structural formula $C_nH_xCl_yF_z$, wherein n is a whole number from 1 to 2 and x, y and z is equal to 2n+2 can be employed, but, of course, are not preferred in view of their known environmental effects. Additionally, noncondensable gases such as carbon dioxide and nitrous oxide and mixtures thereof can be used and are preferred. Additionally, any other propellant capable of dispensing the concentrate known to one of ordinary skill in the art can be used. Mixtures of various propellants and diluents known to one of ordinary skill in the art are often employed to obtain the desired vapor pressure with the container. As will be seen, the propellant can be a separate propellant or can also provide the compressed gas component of the inventive composition.

Typically, the second container 30 includes enough concentrate to prepare approximately two to four batches of the composition.

To prepare the inventive composition, the first container 20 is inverted and the stem 24 is placed adjacent the stem 34 of the second container as shown in FIG. 2. To assist in aligning the stem 24 and the stem 34 a guide 40 is provided. This guide 40 extends over a portion of the stems 24 and 34 when the stems are adjacent one another as shown in FIGS. 2 and 3. To further assist in the alignment of the valve stems, as shown in FIG. 3, one stem can include a male configuration and the other stem can include a female configuration. When the two stems 24 and 34 are adjacent one another, pressure is applied to open the valves 22 and 32. Since the second container 30 includes a propellant such as compressed gas, concentrate is transferred from the second container to the first container. In preferred embodiments, the concentrate remains substantially free from foaming when transferred. When the transfer is complete, the pressure is released and the valves return to there normally seated and closed position. To assist in the transfer of the appropriate amount of concentrate from the second container 30 to the first container 20, the first container can include graduated markings 50 as shown in FIG. 1. The translucency or transparency of the first container allows a user to observe the level of the contents of the first container and discontinue transfer when the appropriate level has been reached. The first container 20 can then be agitated to thoroughly mix the concentrate and diluent.

In an additional method of preparing the inventive composition, the first container 20 also includes compressed gas therein. In such an embodiment, the pressure of the second container 30 must be greater than that of the first container 20 to allow for transfer of the concentrate into the first container. Transfer of the concentrate to the first container then occurs as described above.

In an alternative method, the first container is provided with a resilient filling closure 60 as shown in FIG. 5. This resilient filling closure 60 is shown in the closed position, but includes a passage therethrough which is normally closed due to the resiliency of the filling closure. To effect a transfer of the concentrate from the second container 30 to the first container 20, the valve stem 34 of the second container is inserted into the resilient filling closure 60, thereby opening the passage therein, and pressure is applied to effect transfer. As above, the transfer of concentrate continues until the appropriate amount of concentrate is transferred to the first container.

An alternative method of preparing the inventive composition includes providing a first container 20 having a removable cap 55 as shown in FIG. 5. When preparing the composition, the cap is removed from the first container and diluent is added. Preferably, the diluent is chilled to about 40° F. to reduce the likelihood of foaming of the composition during preparation. The proper amount of concentrate is transferred into the open container from the second container 30. After the appropriate amount of concentrate has been transferred, a gas-producing substance is added to the first container and the container is closed with the cap 55. The first container can then be agitated to mix the contents.

The gas-producing substance can be in the form of a liquid, gel or solid. Preferably, the gas-producing substance is an effervescing tablet of sodium bicarbonate and citric acid or sodium bicarbonate and sodium citrate.

Alternatively, the gas-producing substance can be added to the first container before the concentrate is introduced. In preparing the composition, various additives can be included in either the concentrate or in the diluent, or can be added to the first container by various methods known to one of ordinary skill in the art.

The composition is dispensed from the first container 20 through the valve 22. The valve can be actuated by downward or angular (lateral) pressure. The first container should preferably be used in the inverted position as shown in FIG. 1. Alternative manners of attaching the dispensing container to a vertical surface are shown in FIGS. 6 and 7. FIG. 6 shows a first container in a rack 65 which can be placed over shower head or peg-like protrusion. FIG. 7 shows the first container 20 enclosed in a dispenser 70 that includes a removable top 72. Alternative mounting arrangements known to one of ordinary skill in the art can also be used.

The composition is dispensed from the first container as a creamy, rich foam which exhibits multiple sequential stages or levels of foam. The initial stage of foam where the utilitarian constituent is foamed by the compressed gas on dispensing has a density of about 0.15–0.90 g/cc. In preferred embodiments, the initial stage of foam has a density of about 0.15–0.30 g/cc. The second stage of foam resulting from the vaporizing post-foaming agent has a density of about 0.04–0.30 g/cc. Preferred embodiments exhibit a second stage of foam having a density of about 0.05–0.10 g/cc. Additional stages of foam are possible including a stage of foam resulting from agitation of the composition on a surface to be cleaned, thereby entraining atmospheric air in the utilitarian constituent. These multiple stages or levels of foam provide for extended foam character and less repeated use of the composition during the grooming or cleaning process.

EXAMPLES

Several examples of inventive compositions suitable for use as personal-care products are discussed below. All of the percentages are weight percentages.

Example 1

| CONSTITUENT | % |
| --- | --- |
| Concentrate: | |
| Carbopol ETD 2020 (Thickener) | 1.50 |
| Plantaren PS300 | 30.00 |
| Ammonium Lauryl Sulfate, Decyl Polyglucose | |
| Isobutane | 2.00 |
| Isopentane | 8.00 |
| Water | 58.50 |
| Diluent: | |
| Carbonated Water | 98.50 |
| Triethanolamine (TEA) | 1.50 |
| ***** | |
| Dilution Ratio: | |
| Concentrate | 33.00 |
| Diluent | 66.00 |

The composition of Example 1 appears thick prior to dispensing—having a viscosity on the order of 8,000 cps and an initial pressure of about 39 psig. The composition is dispensed as a dense, continuous initial-stage foam body which post-foamed upon spreading. The foam produced upon post-foaming had an increased volume, was less-dense and was of a lacy character. Such lacy foam character makes this composition suitable for use as a shampoo or similar product.

Example 2

| CONSTITUENT | % |
| --- | --- |
| Concentrate: | |
| Plantaren PS200 | 30.00 |
| Sodium Laureth Sulfate, Decyl Polyglucose | |
| Guar Hydroxypropyl Trimonium Chloride (thickener/conditioning agent) | 1.00 |
| Citric Acid (acidulant) | 0.10 |
| Isobutane | 3.00 |
| Isopentane | 7.00 |
| Water | 58.90 |
| Diluent: | |
| Carbonated Water | 100.00 |
| ***** | |
| Dilution Ratio: | |
| Concentrate | 30.00 |
| Diluent | 70.00 |

The composition of Example 2 appears thick prior to dispensing—having a viscosity on the order of 8,000 cps and an initial pressure of about 41 psig. The composition is dispensed as a dense, continuous initial-stage foam body which post-foamed upon spreading. The foam produced upon post-foaming had an increased volume, was less-dense and was of a slippery and lubricous character. Such foam qualities make the composition useful for shaving.

Example 3

| CONSTITUENT | % |
| --- | --- |
| Concentrate: | |
| Carbopol ETD 2020 (thickener) | 1.75 |
| Plantaren PS300 | 25.00 |
| Ammonium Lauryl Sulfate, | |
| Decyl Polyglucose | |
| Polysorbate-20 (viscosity modifier) | 10.00 |
| Triethanolamine (TEA) | 0.10 |
| -(alkali to neutralize Carbopol) | |
| Ammonium Lauryl Sulfate | 30.00 |
| Isobutane | 4.00 |
| Isopentane | 5.00 |
| Water | 24.15 |
| Diluent: | |
| Water | 96.50 |
| Sodium Bicarbonate | 2.30 |
| Citric Acid | 1.20 |
| ***** | |
| Dilution Ratio: | |
| Concentrate | 50.00 |
| Diluent | 50.00 |

The composition of Example 3, prior to dispensing, is somewhat thinner than the previous examples—having viscosity on the order of 4,000 cps and an initial pressure of about 40 psig. The composition is dispensed as a relatively dense, continuous initial-stage foam body, which, upon spreading, is observed to post-foam to a less-dense second-stage foam of significantly increased volume and thick, airy, lacy character. This composition is useful as a shaving product providing a foam of somewhat thinner foam character than the foam provided by the composition of Example 2.

Example 4

| CONSTITUENT | % |
| --- | --- |
| Concentrate: | |
| Carbopol ETD 2020 (thickener) | 1.25 |
| Plantaren PS300 | 20.00 |
| Ammonium Lauryl Sulfate, | |
| Decyl Polyglucose | |
| Hexylene Glycol (viscosity modifier) | 2.00 |
| PEG-7 Glycerol Cocoate (emollient) | 2.00 |
| Dimethicone Copolyol Eicosanate | 3.00 |
| -(emollient) | |
| Triethanolamine (TEA) | 0.10 |
| -(alkali to neutralize Carbopol) | |
| Ammonium Lauryl Sulfate | 25.00 |
| Polymethoxy Bicyclic Oxazolidine | 0.60 |
| -(preservative) | |
| Isobutane | 3.00 |
| Isopentane | 9.00 |
| Water | 34.05 |
| Diluent: | |
| Water | 98.25 |
| Sodium Bicarbonate | 1.15 |
| Citric Acid | 0.60 |
| ***** | |
| Dilution Ratio: | |
| Concentrate | 40.00 |
| Diluent | 60.00 |

The composition of Example 4, prior to dispensing, is also somewhat thinner than Examples 1 and 2—having a viscosity believed to be on the order of 6,000 cps and an initial pressure of about 24 psig. The composition is dispensed as a relatively dense, continuous initial-stage foam body, which, upon spreading, is observed to post-foam to a less-dense, second-stage soft emollient lather of very significantly increased volume. This composition is suitable for use as a shower cleanser or the like.

Example 5

| CONSTITUENT | % |
| --- | --- |
| Concentrate: | |
| Carbopol ETD 2020 | 1.60 |
| Plantaren PS300 | 25.00 |
| Ammonium Lauryl Sulfate, | |
| Decyl Polyglucose | |
| Hexylene Glycol (viscosity modifier) | 1.00 |
| PEG-7 Glycerol Cocoate (emollient) | 1.00 |
| Dimethicone Copolyol Eicosanate | |
| -(emollient) | 2.00 |
| Triethanolamine (TEA) | 0.40 |
| -(alkali to neutralize Carbopol) | |
| Ammonium Lauryl Sulfate | 15.00 |
| Ammonium Cocoyl Isethioniate | 10.00 |
| Polymethoxy Bicyclic Oxazolidine | 0.60 |
| -(preservative) | |
| Isobutane | 2.00 |
| Isopentane | 8.00 |
| Water | 33.40 |
| Diluent: | |
| Water | 98.25 |
| Sodium Bicarbonate | 1.15 |
| Citric Acid | 0.60 |
| ***** | |
| Dilution Ratio: | |
| Concentrate | 33.00 |
| Diluent | 66.00 |

The composition of Example 5, prior to dispensing, has a viscosity approximating that of Example 4 and an initial pressure of about 26 psig. The composition is dispensed as a relatively dense, continuous initial-stage foam body, which, upon spreading, post-foams to a less-dense, soft, smooth, second-stage emollient lather of significantly increased volume. The composition is useful as a shower cleanser or the like.

Example 6

| CONSTITUENT | % |
| --- | --- |
| Concentrate: | |
| Citric Acid | 0.30 |
| Plantaren PS300 | 40.00 |
| Ammonium Lauryl Sulfate, | |
| Decyl Polyglucose | |
| Soyamidopropyl Betaine | 15.00 |
| Isobutane | 4.00 |
| Isopentane | 4.00 |
| Water | 36.70 |
| Diluent: | |
| Water | 98.25 |
| Sodium Bicarbonate | 1.15 |
| Citric Acid | 0.60 |
| ***** | |

-continued

| CONSTITUENT | % |
| --- | --- |
| Dilution Ratio: | |
| Concentrate | 25.00 |
| Diluent | 75.00 |

The composition of Example 6, prior to dispensing, is thinner than any of the other examples. The composition had an initial pressure of about 30 psig. The composition is dispensed as a continuous initial-stage foam body of lesser density than the initial-stage foams of the other examples; upon spreading, post-foaming occurs and produces a rich, dense, extended second-stage foam which is usable as a shampoo. Example 6 exhibits less post-foaming than the other examples.

Example 7

| CONSTITUENT | % |
| --- | --- |
| Concentrate: | |
| Citric Acid (acidulant) | 0.20 |
| Plantaren PS300 Ammonium Lauryl Sulfate, Decyl Polyglucose | 30.00 |
| Soyamidopropyl Betaine | 2.00 |
| Hydroxypropyl Methylcellulose -(thickener) | 0.50 |
| Isobutane | 3.00 |
| Isopentane | 6.00 |
| Water | 58.30 |
| Diluent: | |
| Water | 98.25 |
| Sodium Bicarbonate | 1.15 |
| Citric Acid | 0.60 |
| ***** | |
| Dilution Ratio: | |
| Concentrate | 20.00 |
| Diluent | 80.00 |

The composition of Example 7, prior to dispensing, is thicker than those of Examples 4 and 5, but thinner than those of Examples 1 and 2. The composition had an initial pressure of about 32 psig. The composition is dispensed as a dense, continuous initial-stage foam body which post-foamed upon spreading. The foam produced upon post-foaming had an increased volume, was less-dense and was of rich, lubricous character. Such composition is suitable for use as a shampoo.

Example 8

| CONSTITUENT | % |
| --- | --- |
| Concentrate: | |
| Carbopol ETD 2020 | 1.60 |
| Plantaren PS300 Ammonium Lauryl Sulfate, Decyl Polyglucose | 25.00 |
| Hexylene Glycol (viscosity modifier) | 1.00 |
| PEG-7 Glycerol Cocoate (emollient) | 1.00 |
| Dimethicone Copolyol Eicosanate -(emollient) | 2.00 |
| Triethanolamine (TEA) | 0.40 |
| -(alkali to neutralize Carbopol) | |
| Ammonium Lauryl Sulfate | 15.00 |
| Ammonium Cocoyl Isethioniate | 10.00 |
| Polymethoxy Bicyclic Oxazolidine -(preservative) | 0.60 |
| Isobutane | 2.00 |
| Isopentane | 8.00 |
| Water | 33.40 |
| Diluent: | |
| Water | 96.50 |
| Sodium Bicarbonate | 2.30 |
| Citric Acid | 1.20 |
| ***** | |
| Dilution Ratio: | |
| Concentrate | 33.00 |
| Diluent | 66.00 |

The composition of Example 8, prior to dispensing, has a viscosity similar to that of the compositions of Examples 4 and 5 and an initial pressure of about 46 psig. The composition is dispensed as a relatively dense, continuous initial-stage foam body, which, upon spreading, post-foams to a less-dense, rich, lubricous second-stage lather of significantly increased volume. This preferred composition is useful as a shower cleanser or the like. The composition is most highly preferred when prepared at the factory as a product ready for dispensing without the need for any mixing of concentrate and diluent by the user.

Example 9

| CONSTITUENT | % |
| --- | --- |
| Concentrate: | |
| Carbopol ETD 2020 (thickener) | 1.75 |
| Plantaren PS300 Ammonium Lauryl Sulfate, Decyl Polyglucose | 25.00 |
| Polysorbate-20 (viscosity modifier) | 10.00 |
| Triethanolamine (TEA) -(alkali to neutralize Carbopol) | 0.10 |
| Ammonium Lauryl Sulfate | 30.00 |
| Isobutane | 4.00 |
| Isopentane | 5.00 |
| Water | 24.15 |
| Diluent: | |
| Water | 96.50 |
| Sodium Bicarbonate | 2.30 |
| Citric Acid | 1.20 |
| ***** | |
| Dilution Ratio: | |
| Concentrate | 30.00 |
| Diluent | 70.00 |

The composition of Example 9, prior to dispensing, has a viscosity on the order of 5,000 cps and an initial pressure of about 56 psig. It is dispensed as a relatively dense, continuous initial-stage foam body, which, upon spreading, is observed to post-foam to a less-dense, second-stage lacy, airy lather of significantly increased volume. This composition is useful as a shaving product.

These examples represent a few of the possible formulations of the inventive post-foamable foam compositions and discuss only a few of the possible uses for these compositions.

While the principles of this invention have been described in connection with specific embodiments, it should be understood clearly that these descriptions are made only by way of example and are not intended to limit the scope of the invention.

I claim:

1. A low-pressure multiple-sequential-foaming composition to be dispensed from a suitable container at pressures between about 10–60 psig in the form of an initial-stage continuous foam body of post-foamable foam which, upon subsequent spreading action, post-foams to form a second stage of a substantially greater level of post-foamed foam, including:

about 0.1–60% by weight of a foamable, post-foamable utilitarian constituent including a surface active agent selected from the group consisting of nonionic, anionic, amphoteric and cationic surfactants and mixtures thereof, such constituent having a viscosity sufficient for dispensing as an initial-stage continuous foam body with a foam density of about 0.15–0.9 g/cc;

about 16.0–99.4% by weight of water;

about 0.50–24% by weight of a volatile liquid post-foaming agent selected from the group consisting of saturated aliphatic hydrocarbons, halogenated hydrocarbons and mixtures thereof, for post-foaming the initial-stage continuous foam body upon spreading to an extended second-stage foam exhibiting a reduced density of about 0.04–0.30 g/cc, the post-foaming agent having a vapor pressure low enough such that it is dispensed substantially as a liquid with the utilitarian constituent; and a compressed gas in an amount sufficient (a) to provide the composition, when contained, with dispensing pressure of about 10–60 psig and (b) to dispense the composition as said initial-stage continuous foam body;

whereby, upon dispensing, the composition exits the container initially as an initial-stage continuous foam body of spreadable foam which, upon spreading, post-foams to a substantially extended foam exhibiting a lower density.

2. The composition of claim 1 wherein the compressed gas is selected from the group consisting of carbon dioxide, nitrous oxide, nitrogen, argon, neon, krypton, xenon, helium and mixtures thereof.

3. The composition of claim 1 wherein the liquid post-foaming agent has a vapor pressure of about 6–14 psig at 90 to 100° F.

4. The composition of claim 1 wherein the initial stage of post-foamable foam has a density of about 0.15–0.30 g/cc, thereby exhibiting 70–85% by volume of undissolved dispersed gas within the post-foamable foam.

5. The composition of claim 1 wherein the second stage of post-foamable foam has a density of about 0.05–0.10 g/cc, thereby exhibiting 90–95% by volume of undissolved dispersed gas within the foamable post-foamed utilitarian constituent.

6. The composition of claim 1 wherein the dispensing pressure of the compressed gas is between about 10 psig and 35 psig.

7. The composition of claim 1 wherein the container consists of clear or translucent plastic.

8. The composition of claim 1 wherein the post-foaming agent comprises a mixture of isopentane and isobutane.

9. A low-pressure multiple-sequential-foaming composition to be dispensed from a suitable container at pressures between about 10–60 psig in the form of an immediately-forming initial-stage of post-foamable foam which, upon subsequent spreading action, post-foams to form a second stage of a substantially greater level of post-foamed foam, including:

about 0.1–60% by weight of a foamable, post-foamable utilitarian constituent including a surface active agent selected from the group consisting of nonionic, anionic, amphoteric and cationic surfactants and mixtures thereof, for dispensing as an immediately-forming initial-stage foam with a foam density of about 0.15–0.9 g/cc;

about 16.0–99.4% by weight of water;

about 0.50–24% by weight of a volatile liquid post-foaming agent selected from the group consisting of saturated aliphatic hydrocarbons, halogenated hydrocarbons and mixtures thereof, for post-foaming the immediately-forming initial-stage foam upon spreading to an extended second-stage foam exhibiting a reduced density of about 0.04–0.30 g/cc, the post-foaming agent having a vapor pressure low enough such that it is dispensed substantially as a liquid with the utilitarian constituent; and a compressed gas in an amount sufficient (a) to provide the composition, when contained, with dispensing pressure of about 10–60 psig and (b) to dispense the composition as said immediately-forming initial-stage foam;

whereby, upon dispensing, the composition exits the container initially as an immediately-forming initial-stage foam of spreadable foam which, upon spreading, post-foams to a substantially extended foam exhibiting a lower density.

10. The composition of claim 9 wherein the initial stage of post-foamable foam has a density of about 0.15–0.30 g/cc, thereby exhibiting 70–85% by volume of undissolved dispersed gas within the post-foamable foam.

11. The composition of claim 9 wherein the second stage of post-foamable foam has a density of about 0.05–0.10 g/cc, thereby exhibiting 90–95% by volume of undissolved dispersed gas within the foamable post-foamed utilitarian constituent.

12. The composition of claim 9 wherein the dispensing pressure of the compressed gas is between about 10 psig and 35 psig.

13. A multiple-secuential-foaming cleansing or cosmetic composition dispensed from a suitable container by a compressed gas, at a dispensing pressure of about 10–60 psig in the form of a post-foamable foam comprising:

a dispensed initial-stage continuous foam body of post-foamable foam formed immediately upon dispensing by the compressed gas as the composition is dispensed from the container, the initial-stage continuous foam body of post-foamable foam exhibiting a density of about 0.15–0.90 g/cc and comprising a liquid aqueous mixture consisting essentially of:

about 10–85% by volume of dispersed gas;

a foamable, post-foamable utilitarian constituent; and a volatile liquid post-foaming agent selected from the group consisting of saturated aliphatic hydrocarbons, halogenated hydrocarbons and mixtures thereof, for post-foaming the initial-stage continuous foam body upon spreading and having a vapor pressure low enough within the dispensed initial-stage post-foamable foam to remain essentially as a liquid with the utilitarian constituent until subsequent spreading action; and a second stage of a substantially greater volume of post-foamed foam formed essentially by vaporization of the post-foaming agent upon spreading, the second stage of foam exhibiting a lower density of about 0.04–0.3 g/cc and consisting of about 70–96% by volume of dispersed gas within the foamable post-foamed utilitarian constituent.

14. The composition of claim 13 wherein the foamable utilitarian constituent includes a surface active agent selected from the group consisting of nonionic, anionic, amphoteric and cationic surfactants and mixtures thereof.

15. The composition of claim 14 wherein the utilitarian constituent includes a diluent.

16. The composition of claim 13 wherein the compressed gas is selected from the group consisting of carbon dioxide, nitrous oxide, nitrogen, argon, neon, krypton, xenon, helium and mixtures thereof.

17. The composition of claim 13 wherein the liquid post-foaming agent has a vapor pressure of about 6–14 psig at 90 to 100° F.

18. The composition of claim 13 wherein the initial stage of post-foamable foam has a density of about 0.15–0.30 g/cc, thereby exhibiting 70–85% by volume of undissolved dispersed gas within the post-foamable foam.

19. The composition of claim 13, wherein the second stage of post-foamable foam has a density of about 0.05–0.10 g/cc, thereby exhibiting 90–95% by volume of undissolved dispersed gas within the foamable post-foamed utilitarian constituent.

20. The composition of claim 13 wherein the dispensing pressure of the compressed gas is between about 10 psig and 35 psig.

21. The composition of claim 13 wherein the container consists of clear or translucent plastic.

22. The composition of claim 13 wherein the post-foaming agent comprises a mixture of isopentane and isobutane.

23. A multiple-sequential-foaming cleansing or cosmetic composition dispensed from a suitable container by a compressed gas, at a dispensing pressure of about 10–60 psig in the form of a post-foamable foam comprising:
    a dispensed immediately-forming initial-stage of post-foamable foam formed immediately upon dispensing by the compressed gas as the composition is dispensed from the container, the immediately-forming initial-stage of post-foamable foam exhibiting a density of about 0.15–0.90 g/cc and comprising a liquid aqueous mixture consisting essentially of:
    about 10–85% by volume of dispersed gas;
    a foamable, post-foamable utilitarian constituent; and
    a volatile liquid post-foaming agent selected from the group consisting of saturated aliphatic hydrocarbons, halogenated hydrocarbons and mixtures thereof, for post-foaming the immediately-forming initial-stage foam upon spreading and having a vapor pressure low enough within the dispensed initial-stage post-foamable foam to remain essentially as a liquid with the utilitarian constituent until subsequent spreading action; and
    a second stage of a substantially greater volume of post-foamed foam formed essentially by vaporization of the post-foaming agent upon spreading, the second stage of foam exhibiting a lower density of about 0.04–0.3 g/cc and consisting of about 70–96% by volume of dispersed gas within the foamable post-foamed utilitarian constituent.

24. The composition of claim 23 wherein the initial stage of post-foamable foam has a density of about 0.15–0.30 g/cc, thereby exhibiting 70–85% by volume of undissolved dispersed gas within the post-foamable foam.

25. The composition of claim 23 wherein the second stage of post-foamable foam has a density of about 0.05–0.10 g/cc, thereby exhibiting 90–95% by volume of undissolved dispersed gas within the foamable post-foamed utilitarian constituent.

26. The composition of claim 23 wherein the dispensing pressure of the compressed gas is between about 10 psig and 35 psig.

27. A low-pressure multiple-sequential-foaming composition to be dispensed from a plastic container at pressures of below about 60 psig as an initial-stage continuous foam body and which post-foams upon spreading, to a second stage of foam, including:
    about 0.1–60% by weight of a thickened aqueous foamable utilitarian constituent, such constituent having a viscosity sufficient for dispensing as an initial-stage continuous foam body with a foam density of about 0.15–0.9 g/cc;
    about 16.0–99.4% by weight of water;
    about 0.50–24% by weight of a volatile liquid post-foaming agent selected from the croup consisting of saturated aliphatic hydrocarbons, halogenated hydrocarbons, and mixtures thereof dispensable with the utilitarian constituent for post-foaming the initial-stage continuous foam body upon spreading to an extended second-stage foam exhibiting a reduced density of about 0.04–0.3 g/cc, the post-foaming agent having a vapor pressure low enough such that it is dispensed substantially as a liquid with the utilitarian constituent; and
    a compressed gas selected from the group consisting of carbon dioxide, nitrous oxide, nitrogen, argon, neon, kryoton, xenon, helium and mixtures thereof in an amount sufficient (a) to provide the composition, when contained, with dispensing pressure of below about 60 psig and (b) to dispense the composition as said initial-stage continuous foam body;
    whereby, upon dispensing, the composition exits the container initially as an initial-stage continuous foam body of spreadable foam with a density of about 0.15–0.9 g/cc which post-foams upon spreading to a substantially extended foam exhibiting a lower density of about 0.04–0.3 g/cc.

28. The composition of claim 27 wherein the foamable utilitarian constituent includes a surface active agent selected from the group consisting of nonionic, anionic, amphoteric and cationic surfactants and mixtures thereof.

29. The composition of claim 27 wherein the initial stage of post-foamable foam has a density of about 0.15–0.30 g/cc, thereby exhibiting 70–85% by volume of undissolved dispersed gas within the post-foamable foam.

30. The composition of claim 27 wherein the second stage of post-foamable foam has a density of about 0.05–0.10 g/cc, thereby exhibiting 90–95% by volume of undissolved dispersed gas within the foamable post-foamed utilitarian constituent.

31. The composition of claim 27 wherein the dispensing pressure of the compressed gas is between about 10 psig and 35 psig.

32. The composition of claim 27 wherein the container consists of clear or translucent plastic.

33. The composition of claim 27 wherein the post-foaming agent comprises a mixture of isopentane and isobutane.

34. The composition of claim 27 wherein the liquid post-foaming agent has a vapor pressure of about 6–14 psig at 90 to 100° F.

35. A low-pressure multiple-sequential-foaming composition to be dispensed from a plastic container at pressures of below about 60 psig as an immediately-forming initial-stage foam and which post-foams upon spreading, to a second stage of foam, including:

about 0.1–60% by weight of a thickened aqueous foamable utilitarian constituent, for dispensing as an immediately-forming initial-stage foam with a foam density of about 0.15–0.9 g/cc;

about 16.0–99.4% by weight of water;

about 0.50–24% by weight of a volatile liquid post-foaming agent selected from the group consisting of saturated aliphatic hydrocarbons, halogenated hydrocarbons, and mixtures thereof dispensable with the utilitarian constituent for post-foaming the immediately-forming initial-stage foam upon spreading to an extended second-stage foam exhibiting a reduced density of about 0.04–0.3 g/cc, the post-foaming agent having a vapor pressure low enough such that it is dispensed substantially as a liquid with the utilitarian constituent; and a compressed gas selected from the group consisting of carbon dioxide, nitrous oxide, nitrogen, argon, neon, krypton, xenon, helium and mixtures thereof in an amount sufficient (a) to provide the composition, when contained, with dispensing pressure of below about 60 psig and (b) to dispense the composition as said immediately-forming initial-stage foam;

whereby, upon dispensing, the composition exits the container initially as an immediately-forming initial-stage of spreadable foam with a density of about 0.15–0.9 g/cc which post-foams upon spreading to a substantially extended foam exhibiting a lower density of about 0.04–0.3 g/cc.

36. The composition of claim 35 wherein the initial stage of post-foamable foam has a density of about 0.15–0.30 g/cc, thereby exhibiting 70–85% by volume of undissolved dispersed gas within the post-foamable foam.

37. The composition of claim 35 wherein the second stage of post-foamable foam has a density of about 0.05–0.10 g/cc, thereby exhibiting 90–95% by volume of undissolved dispersed gas within the foamable post-foamed utilitarian constituent.

38. The composition of claim 35 wherein the dispensing pressure of the compressed gas is between about 10 psig and 35 psig.

* * * * *

UNITED STATES PATENT AND TRADEMARK OFFICE
CERTIFICATE OF CORRECTION

PATENT NO. : 5,902,225
DATED : May 11, 1999
INVENTOR(S) : James A. Monson

It is certified that error appears in the above-identified patent and that said Letters Patent is hereby corrected as shown below:

At Column 4, line 55, after "composition is diluent.", insert the following sentence:
--The principal "active" ingredient(s) and any diluents, thickeners and/or other additives should be selected such that the utilitarian constituent has a viscosity sufficient for dispensing as a continuous foam body with post-foaming substantially restrained prior to the spreading occurring during use of the composition.--

At column 4, line 67, change "%" to -- --.
At column 6, line 14, change "here" to -- where --.
At column 6, line 16, change "referably" to -- preferably --.
At column 7, line 8. After "when it is contained.", insert the following paragraph and table:
--Table 1 shows the pressure ranges of a typical end-user form of the composition over the useful life of the product. The data are for the composition of Example 8 below.

TABLE 1

| Product Life | Pressure (psig) | Foam density (g/cm$^3$) dispensed | Foam density (g/cm$^3$) spread |
|---|---|---|---|
| Freshly made | 46.0 | 0.18 | 0.07 |
| Aged 10 months No product dispensed | 32.4 | *** | *** |
| Aged 10 months First third dispensed | 29.3 | 0.20 | 0.08 |
| Aged 10 months Middle third dispensed | 21.3 | 0.18 | 0.09 |
| Aged 10 months Final third dispensed | 15.4 | 0.18 | 0.08 |

As indicated by the data above, a preferred pressure range is from about 15 to about 50 psig.--

UNITED STATES PATENT AND TRADEMARK OFFICE
CERTIFICATE OF CORRECTION

PATENT NO. : 5,902,225

DATED : May 11, 1999

INVENTOR(S) : James A. Monson

It is certified that error appears in the above-identified patent and that said Letters Patent is hereby corrected as shown below:

At column 9, line 61, after "about 0.05-0.10 g/cc.", insert the following sentence:
--Table 1 shows the foam density ranges of the composition of Example 8 -- a composition typical of the invention.--
At column 16, line 46, Change "secuential" to -- sequential --.
At column 18, line 24, change "croup" to -- group --.

Signed and Sealed this

Twenty-eighth Day of December, 1999

Q. TODD DICKINSON

Attest:

Attesting Officer

Acting Commissioner of Patents and Trademarks